United States Patent [19]

Kleemann et al.

[11] Patent Number: 4,828,766
[45] Date of Patent: May 9, 1989

[54] PROCESS FOR THE PREPARATION OF VINYLDIPHOSPHONIC ACID AND SALTS THEREOF

[75] Inventors: Stephan Kleemann, Schriesheim; Werner Ehret, Wilhelmsfeld, both of Fed. Rep. of Germany

[73] Assignee: Benckiser-Knapsack GmbH, Ladenburg, Fed. Rep. of Germany

[21] Appl. No.: 67,885

[22] Filed: Jun. 30, 1987

[30] Foreign Application Priority Data

Jul. 7, 1986 [DE] Fed. Rep. of Germany ....... 3622786

[51] Int. Cl.$^4$ ................ C07F 9/38; C07C 51/09; C07C 53/08; C07C 53/122
[52] U.S. Cl. ................ 260/502.4 P; 562/606; 562/607
[58] Field of Search ............... 260/502.4 A, 502.4 R, 260/502.4 P

[56] References Cited

U.S. PATENT DOCUMENTS

| | | | |
|---|---|---|---|
| 2,708,204 | 5/1955 | Bell et al. | 558/167 |
| 3,062,792 | 11/1962 | McConnell et al. | 260/85.5 |
| 3,400,147 | 9/1968 | Rogovin et al. | 260/502.4 A |
| 3,468,935 | 9/1969 | Peck | 260/502.4 A |
| 4,332,736 | 6/1982 | Starner et al. | 260/502.4 A |
| 4,386,036 | 5/1983 | Kleiner | 260/502.4 R |
| 4,388,252 | 1/1983 | Dursch et al. | 260/502.4 P |
| 4,493,803 | 1/1985 | Kleiner et al. | 260/502.4 R |

FOREIGN PATENT DOCUMENTS 2108042 11/1971 Fed. Rep. of Germany .
1204967 9/1970 United Kingdom .

OTHER PUBLICATIONS

Canavan et al., "J. Chem. Soc." (Jan. 1952) pp. 331–334.

Primary Examiner—J. E. Evans
Attorney, Agent, or Firm—Foley & Lardner, Schwartz, Jeffery, Schwaab, Mack, Blumenthal & Evans

[57] ABSTRACT

An improved process for the preparation of vinyldiphosphonic acid is disclosed. The process involves elimination of a volatile acid from a 1-(O-acyl)-ethane-1,1-diphosphonic acid. The starting materials may be prepared by reacting 1-hydroxyethane-1,1-diphosphonic acid with the corresponding acid or directly by reacting the acid with phosphorous acid and an acyl anhydride.

15 Claims, No Drawings

1 …

PROCESS FOR THE PREPARATION OF VINYLDIPHOSPHONIC ACID AND SALTS THEREOF

The present invention relates to an improved process for the preparation of vinyldiphosphonic acid and salts thereof from industrially readily available, economical intermediates.

Lower alkylene-1,1-diphosphonic acids and salts thereof are known from, for example, British Patent Specification No. 1,204,967. This reference has also disclosed that these compounds have extraordinarily good sequestering and dispersing properties and can therefore be used with great advantage as water-softening agents, stabilizers and additives in soaps and detergents etc., and as additives in a large number of industrial products. These monomeric compounds can also be polymerized either alone or together with other compounds containing vinyl groups, and such polymers have, for example, flameproofing properties. For these possible uses, reference is made especially to the above reference.

According to British Patent Specification No. 1,204,967, vinyldiphosphonic acid and salts thereof are prepared by thermal dehydration of 1-hydroxyethane-1,1-diphosphonic acid or an alkali metal salt thereof, in the presence of other non-oxidizing metal ions, if appropriate, at temperatures from 200° to 500°C. Preferably, a molar metal ion/phosphonic acid ratio of 4:1 to 5:1 is maintained. A repeat of this process shows that, under the parameters given, the vinyldiphosphonic acid content in the end product is below 40%. The nature of the impurities has not been investigated, but spectroscopy shows them to be inhomogeneous, without containing double bonds.

In German Patent No. 2,108,042, a further process for the dehydration of 1-hydroxyethane-1,1-diphosphonic acid or salts thereof is described. By heating these compounds for 10–15 minutes to temperatures of 350°–380° C., an elimination of 0.1–0.8 mol of water per mol of salt is said to take place and a product is said to be formed which contains only a small fraction of ethylenic material (50% at 0.8 mol dehydration, 20% at 0.5 mol dehydration and approximately 0 at 0.2 mol dehydration). Further products formed are said to be condensed phosphates and other products, which is in agreement with our findings above, that these conditions are unsuitable for the preparation of vinyldiphosphonic acid. Thus, according to this state of the art, vinyl-1,1-diphosphonic acid could be obtained only in a poor yield and with involved purification procedures.

SUMMARY OF THE INVENTION

Therefore, it is an object of the present invention to provide a simpler and more economical process for the preparation of vinyl-1,1-diphosphonic acid.

It is a further object of the invention to produce vinyl-1,1-diphosphonic acid of high yield and purity.

It is yet another object of the invention to produce vinyl-1,1-diphosphonic acid at relatively low temperatures.

Surprisingly, it was possible to achieve these and other objects by replacing the hydroxyl group in 1-hydroxyethane-diphosphonic acid with an acyl group. The acyl group is readily eliminated in the form of a volatile acid under relatively mild conditions. Yields of 70–80% are achieved.

DESCRIPTION OF THE PREFERRED EMBODIMENTS

According to the known process, water is eliminated directly from the salts of hydroxyethane-1,1-diphosphonic acid. The elimination takes place to a significant extent only at relatively high temperatures. The high temperatures then evidently promote the formation of byproducts.

In the present invention, the hydroxyl group in 1-hydroxyethane-diphosphonic acid is replaced by an acyl group which can be eliminated more readily. The elimination of a volatile acid, preferably acetic acid, from 1-(O-acyl)-ethane-1,1-diphosphonic acid, preferably from 1-(O-acetyl)-ethane-1,1-diphosphonic acid takes place under relatively mild conditions, i.e., by heating to temperatures of 200°–300° C. Advantageous conversion is obtained at a relatively high purity and with yields of 70-80% of pure vinyldiphosphonic acid. The purity and yield achieved greatly facilitate further processing, in particular polymerization and copolymerization. In contrast to the product of the state of the art, expensive additional enrichment or purification of the monomers may be unnecessary.

The volatile acids which can be used as the leaving group are alkylcarboxylic acids having 1 to 10 carbon atoms, more preferably 2-5 carbon atoms, and especially acetic acid and propionic acid. Other acids, even if they are highly suitable as a "volatile group", are normally less economical and are therefore not preferred.

The 1-acyl-ethane-1,1-diphosphonic acids used as starting materials can be prepared by reacting 1-hydroxyethane-1,1-diphosphonic acid with the corresponding acids or active derivatives thereof, such as esters, or acid chlorides or anhydrides. However, direct preparation from acetic acid, phosphorous acid and an acyl anhydride is particularly preferred. Acetic anhydride is used as the acyl anhydride, in order to avoid mixed reactions.

The thermal conversion of the 1-(O-acyl)-ethane-1,1-diphosphonic acid is preferably carried out in the presence of 4 to 5 moles of alkali or ammonia, so that the corresponding tetraalkali metal salt of vinyldiphosphonic acid is formed. Likewise, the acyl group is bound either as an alkali metal salt or ammonium salt or, due to the high temperatures, is volatilized. The volatilization can also be promoted by carrying out the reaction under a slight vacuum, preferably under 50–500 millibar.

The salts formed can be converted into the free acid form by reaction with strongly acidic ion exchangers, or other metal salts can be prepared by double decomposition. The preferred metal salts are the alkali metal salts, especially sodium and potassium salts, since these have a particularly high water solubility. Calcium, magnesium and other salts, in particular various ammonium salts, can also be advantageous for further processing (in this connection, compare British Patent Specification No. 1,204,967).

The examples which follow are meant to illustrate the invention, but without restricting its scope.

EXAMPLE 1

Reactants:

Phosphorous acid (98.5%)    The quantity data are

-continued

| Reactants: | |
|---|---|
| Acetic anhydride (100%) | to be found in the table which follows |
| Sodium carbonate (100%) | |
| Acetic acid (100%) | |

| 1st charge: | 31% by volume of the acetic acid/phosphorous acid solution |
|---|---|
| Addition I: | 69% by volume of the acetic acid/phosphorous acid solution |
| Addition II: | Acetic anhydride |
| Addition III: | Sodium carbonate |

The phosphorous acid was dissolved in the acetic acid.

Experimental Procedure

In a two-liter reaction vessel with a flat-flange ground joint, provided with a stirrer, thermometer, reflux condenser, two dropping funnels and a graduated solids funnel, the first charge is heated to 120°–130° C. After this temperature has been reached, additions I and II are added dropwise in parallel within one hour. During the addition, steady refluxing is established. The reaction temperature is about 120° C. After the addition has ended, the reaction is allowed to proceed for a further two hours and then addition III is slowly added without heating at a reaction temperature of about 100° C. If a homogeneous solution has not formed after the end of the addition, the mixture is heated to 120°–130° C. until all the sodium carbonate has dissolved. The homogeneous products thus obtained are of varying consistency, depending on the number of sodium ions which they contain per mol of 1-(0-acetyl)-ethane-1,1-diphosphonic acid. With a rising number of sodium ions, the viscosity increases, and the tetrasodium phosphonate is a viscous paste even at 100° C. to 120° C. The hard sodium phosphonates are reduced to powder by means of a mortar and pestle and are then calcined in two different ways.

Method (a):

The powder in a porcelain dish is statically heated in a muffle furnace. After the desired reaction temperature of about 220° C. has been reached, the phosphonate remains for 1 to 2 hours in the furnace. This gives a slightly frothy colorless product which can readily be reduced to powder.

Method (b):

The powder is introduced into a heated laboratory kneader and melted, and the excess acetic acid and acetic anhydride are removed at 140° C. to 220° C. within about two hours under a slight water pump vacuum. After the solvent has been completely removed, the phosphonate becomes pulverulent. After calcination at 220° to 250° C. for four hours, a colorless powder results.

Various experiments carried out according to the above methods are summarized in Table 1 which follows. The vinyldiphosphonic acid content is determined spectroscopically or by nuclear magnetic resonance measurement.

TABLE 1

| No. Method | in moles | | | | Time Hours | Temp. °C. | Yield % |
|---|---|---|---|---|---|---|---|
| | $H_3PO_3$ | $Ac_2O$ | $CH_3COOH$ | $Na_2CO_3$ | | | |
| 1 a | 4 | 4.4 | 7.2 | 4 | 1 | 220 | 63.5 |
| 2 a | 4 | 4.4 | 7.2 | 4 | 1 | 240 | 66.5 |
| 3 a | 4 | 4.4 | 7.2 | 5 | 1 | 220 | 58.6 |
| 4 b | 4 | 4.8 | 7.2 | 4.5 | 4 | 250 | 62.7 |
| 5 b | 4 | 6.0 | 7.2 | 4 | 4 | 250 | 71.0 |
| 6 b | 4 | 4.8 | 7.2 | 4 | 4 | 250 | 76.2 |
| 7 b | 4 | 5.0 | 7.2 | $4K_2CO_3$ | 4 | 240 | 65.8 |
| 8 a | 4 | 5.0 | 7.2 | $4.4(NH_4)_2CO_3$ | 2 | 220 | 65.1 |
| 9 b | 4 | 5.0 | 7.2 | $2.2(NH_4)_2CO_3$ $2.0Na_2CO_3$ | 4 | 240 | 71.6 |

EXAMPLE 2

20 g of tetrasodium 1-hydroxyethane-1,1-diphosphonate are treated with a 6-fold molar amount of propionic anhydride and, after 100 minutes at 130° C., volatile constituents and excess propionic anhydride are removed under reduced pressure.

Further processing by Method a) (220° C./1 hour) gave 53.7% of vinyldiphosphonic acid. The vinyldiphosphonic acid content was determined by measuring the nuclear magnetic resonance.

EXAMPLE 3

Comparison example (corresponding to Example 1 of German Patent No. 2,108,042)

2 g of a tetrasodium 1-hydroxyethane-1,1-diphosphonate (containing 9.6% by weight of water of crystallization) are heated in a platinum crucible for 32 minutes to 380° C. under a nitrogen atmosphere. The weight loss is 11.4%, equivalent to a loss of 0.32 mol of water/mol of anhydrous tetrasodium diphosphonate. According to nuclear magnetic resonance analysis, the mixture obtained contains 16% of vinyl compounds.

EXAMPLE 4

Comparison example (corresponding to Example 2 of British Patent Specification No. 1,204,967)

5 g of anhydrous 1-hydroxyethane-1,1-diphosphonic acid are mixed with the sodium hydroxide quantity indicated in Table 2 and are heated in an open porcelain dish in a muffle furnace for the times and at the temperatures also given in the table. The resulting product is investigated by nuclear magnetic resonance (31P NMR), thin layer chromatography and IR-spectroscopy. A significant amount of vinyldiphosphonic acid was not formed in any of the experiments shown in the table.

TABLE 2

| Moles NaOH | Temp. | Reaction time | Color of product | Yield |
|---|---|---|---|---|
| 4.5 | 350° C. | 4 hours | off-white* | 0 |
| 4.5 | 450° C. | 4 hours | black* | 0 |
| 4.0 | 350° C. | 4 hours | off-white* | 0 |
| 3.0 | 350° C. | 4 hours | decomposition | 0 |

*partial decomposition, virtually no C=C double bonds are formed according to $^{31}$P NMR, DC and IR.

What is claimed is:

1. A process for forming vinyl-disphosphonic acid and salts thereof, comprising the steps of:

forming 1-(O-acyl)-ethane-1,1-diphosphonic acid; and heating the 1-(O-acyl)-ethane-1,1-diphosphonic acid to about 200–300° C. with or without alkali or ammonia to eliminate an alkylcarboxy acid having from 1 to 10 carbon atoms from the 1-(O-acyl)-ethane-1,1-diphosphonic acid to form vinyl diphosphonic acid when alkali or ammonia is not present or a salt of vinyl diphosphonic acid when alkali or ammonia is present.

2. A process as claimed in claim 1, wherein the acid is an alkylcarboxylic acid having from 2 to 5 carbon atoms.

3. A process as claimed in claim 1, wherein the acid is a member of the group consisting of acetic acid and propionic acid.

4. A process as claimed in claim 1, wherein the 1-(O-acyl)-ethane-1,1-diphosphonic acid is in the form of a salt.

5. A process as claimed in claim 4, wherein the salt is a member of the group consisting of sodium and potassium salts of 1-(O-acyl)-ethane-1,1-diphosphonic acid.

6. A process as claimed in claim 4, wherein the salt is the ammonium salt of 1-(O-acyl)-ethane-1,1-diphosphonic acid.

7. A process as claimed in claim 1, wherein the 1-(O-acyl-ethane-1,1-diphosphonic acid is directly fomed by the reaction of alkylcarboxylic acid, phosphorous acid and an acyl anhydride.

8. A process as claimed in claim 7, wherein the alkylcarboxylic acid is acetic acid.

9. A process as claimed in claim 8, wherein the acyl anhydride is acetic anhydride.

10. A process as claimed in claim 1, wherein the 1-(O-acyl)-ethane-1,1-diphosphonic acid is formed by reacting 1-hydroxyethane-1,1-diphosphonic acid with an alkylcarboxylic acid or derivative.

11. A process as claimed in claim 1, wherein the volatile acid is eliminated in vacuo at a pressure of from about 50 to 500 mbar.

12. A process as claimed in claim 1, wherein the ratio of phosphonic acid group and the corresponding cations is between about 1:1 and 1:2.5.

13. A process as claimed in claim 1, wherein said heating step is carried out in the presence of alkali or ammonia, so that a salt of vinyldiphosphonic acid is formed.

14. A process as claimed in claim 13, wherein 4 to 5 moles of alkali or ammonia is used for each mole of 1(O-acyl)-ethane-1,1-diphosphonic acid.

15. A process as claimed in claim 14, wherein a sodium or potassium salt of vinyldiphosphonic acid is formed.

* * * * *